(12) United States Patent
Rastegar

(10) Patent No.: US 9,168,387 B2
(45) Date of Patent: *Oct. 27, 2015

(54) RESERVE BATTERY OPERATED POWER SUPPLIES

(71) Applicant: Jahangir S Rastegar, Stony Brook, NY (US)

(72) Inventor: Jahangir S Rastegar, Stony Brook, NY (US)

(73) Assignee: OMNITEK PARTNERS LLC, Ronkonkoma, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/070,543

(22) Filed: Nov. 3, 2013

(65) Prior Publication Data

US 2014/0057149 A1 Feb. 27, 2014

Related U.S. Application Data

(62) Division of application No. 13/032,631, filed on Feb. 22, 2011, now Pat. No. 8,588,903.

(51) Int. Cl.
*A61N 1/39* (2006.01)
*H01M 6/32* (2006.01)

(52) U.S. Cl.
CPC .............. *A61N 1/3975* (2013.01); *H01M 6/32* (2013.01); *A61N 1/3993* (2013.01)

(58) Field of Classification Search
CPC ...... A61N 1/3975; A61N 1/3993; H01M 6/32
USPC ...................................... 607/5, 142; 429/118
See application file for complete search history.

(56) References Cited

U.S. PATENT DOCUMENTS

| 5,183,712 | A  | * | 2/1993  | Beldock et al.     | 429/9    |
|-----------|----|---|---------|--------------------|----------|
| 5,985,481 | A  | * | 11/1999 | Champagne et al.   | 429/90   |
| 6,041,255 | A  | * | 3/2000  | Kroll              | 607/5    |
| 6,258,062 | B1 | * | 7/2001  | Thielen et al.     | 604/141  |
| 6,408,206 | B1 | * | 6/2002  | Kroll et al.       | 607/5    |
| 8,135,469 | B2 | * | 3/2012  | Roberts et al.     | 607/35   |
| 8,588,903 | B2 | * | 11/2013 | Rastegar           | 607/5    |
| 8,593,104 | B2 | * | 11/2013 | Rastegar           | 320/105  |
| 2002/0156506 | A1 | * | 10/2002 | Kroll et al.    | 607/5    |
| 2003/0187339 | A1 | * | 10/2003 | Carim            | 600/372  |
| 2004/0116847 | A1 | * | 6/2004  | Wall             | 604/93.01|
| 2009/0216292 | A1 | * | 8/2009  | Pless et al.     | 607/33   |
| 2010/0042171 | A1 | * | 2/2010  | Saketkhou        | 607/5    |
| 2010/0312163 | A1 | * | 12/2010 | Forsell          | 604/9    |
| 2012/0200250 | A1 | * | 8/2012  | Rastegar         | 320/105  |
| 2012/0209185 | A1 | * | 8/2012  | Kamen et al.     | 604/132  |
| 2012/0215270 | A1 | * | 8/2012  | Rastegar         | 607/5    |
| 2013/0197475 | A1 | * | 8/2013  | Dunn             | 604/506  |
| 2014/0057149 | A1 | * | 2/2014  | Rastegar         | 429/118  |

* cited by examiner

*Primary Examiner* — Christopher A Flory

(57) ABSTRACT

A power supply including: a reserve power source for providing power, the reserve power source including: a liquid reserve battery which requires activation to produce power; an activator having a liquid electrolyte for activating the liquid reserve battery upon a mechanical activation such that the liquid electrolyte is forced from the activator into the liquid reserve battery through a communication between the activator and the liquid reserve battery; a pair of terminals operatively connected to the liquid reserve battery for outputting the produced power; and a mechanical stop for preventing the activator from activating the liquid reserve battery, the stop being selectively removable when activation is desired. Where the activator includes a container having the liquid electrolyte contained therein and the activator further includes: a top and a bellow attached on one end to the top and to a portion of the liquid reserve battery at an other end.

12 Claims, 7 Drawing Sheets

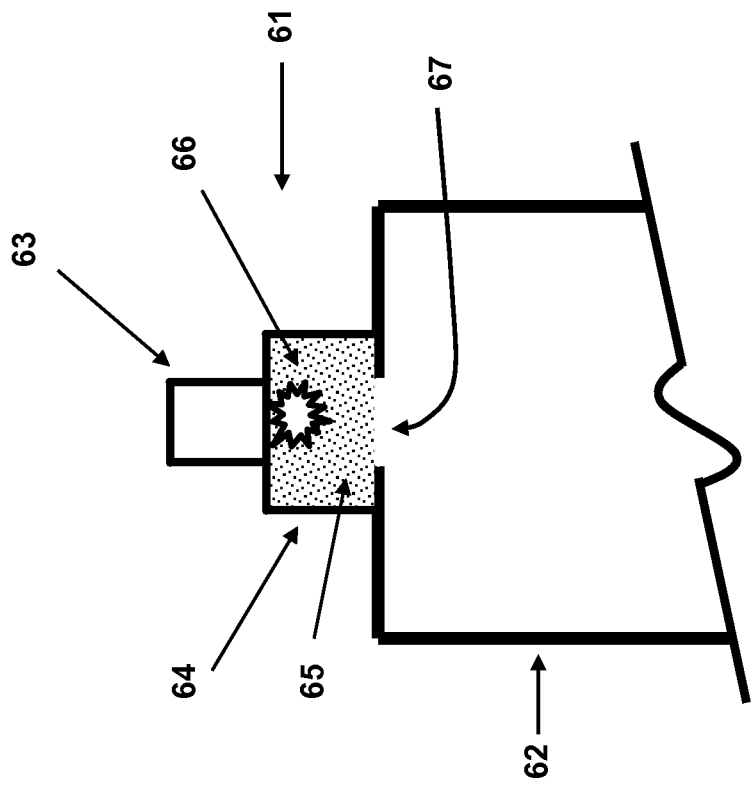
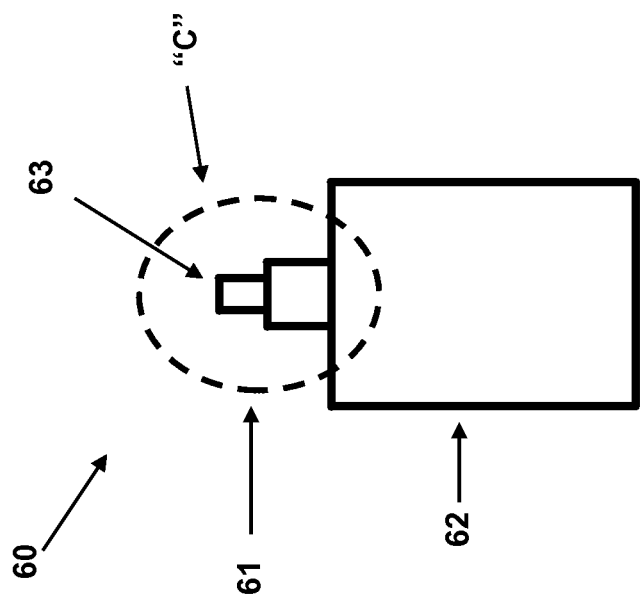
Figure 10
Figure 9

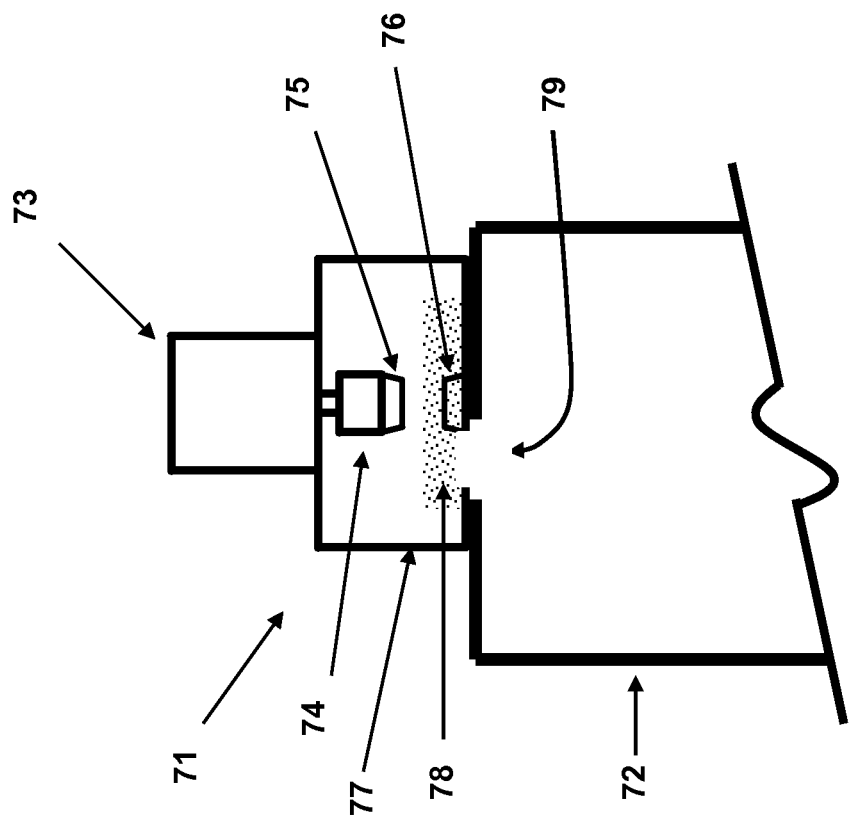
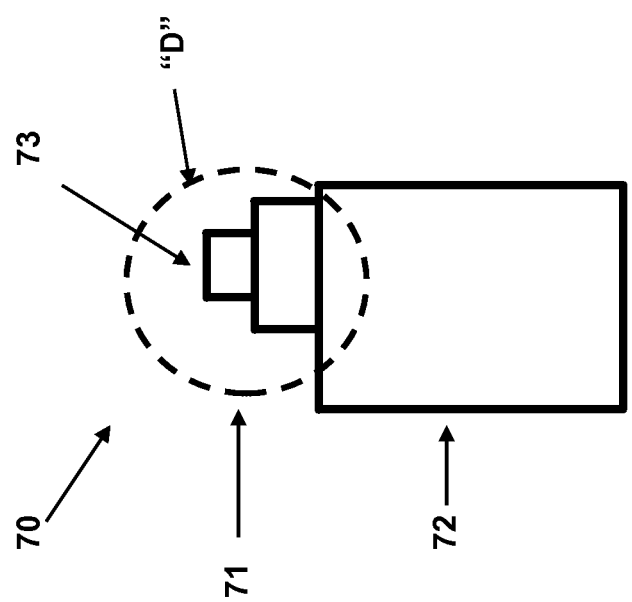
Figure 12
Figure 11

RESERVE BATTERY OPERATED POWER SUPPLIES

CROSS REFERENCE TO RELATED APPLICATION

This application is a Continuation Application of U.S. application Ser. No. 13/032,631 filed on Feb. 22, 2011, the entire contents of which is incorporated herein by reference.

BACKGROUND OF THE INVENTION

1. Field of the Invention

The present invention relates in general to very long lasting reserve power sources for powering devices, such as emergency medical devices and their means of activation and electrical storage and regulation, and more particularly to provide highly reliable reserve power sources for automated external defibrillators and the like.

2. Prior Art

An automated external defibrillator or AED is a portable electronic device that automatically diagnoses the potentially life threatening cardiac arrhythmias of ventricular fibrillation and ventricular fibrillation in a patient, and is able to treat them through defibrillation, the application of electrical therapy which stops the arrhythmia, allowing the heart to reestablish an effective rhythm. AEDs are designed to be simple to use for the layman, and the use of AEDs is taught in many first aid, first responder and basic life support (BLS) level CPR classes. Uncorrected, these cardiac conditions (ventricular tachycardia, ventricular fibrillation, asystole) rapidly lead to irreversible brain damage and death. After approximately three to five minutes, irreversible brain/tissue damage may begin to occur.

An AED is external because the operator applies the electrode pads to the bare chest of the victim, as opposed to internal defibrillators, which have electrodes surgically implanted inside the body of a patient. Automatic refers to the unit's ability to autonomously analyze the patient condition, and to assist this, the vast majority of units have spoken prompts, and some may also have visual displays to instruct the user.

The first commercially available AEDs were all of a monophasic type, which gave a high-energy shock, up to 360 to 400 Joules depending on the model. This caused increased cardiac injury and in some cases second and third-degree burns around the shock pad sites. Newer AEDs have tended to utilize biphasic algorithms which give two sequential lower-energy shocks of 120-200 joules, with each shock moving in an opposite polarity between the pads. This lower-energy waveform has proven more effective in clinical tests, as well as offering a reduced rate of complications and reduced recovery time.

Most manufacturers recommend checking the AED before every period of duty or on a regular basis for fixed units. Some units need to be switched on in order to perform a self check; other models have a self check system built in with a visible indicator.

Almost all portable AEDs, like those mounted on walls of offices, schools, airports, etc., are powered by regular primary or rechargeable batteries. The amount of charge available by such batteries and their performance, however, deteriorates over time. This is particularly a problem with AEDs provided for use in offices, schools and other public and private places, which may be used only once every several years. Such AEDs may very seldom be tested to ensure that their batteries can still be fully functional and the tests without the full load may not be reliable.

For an emergency medical device such as an AED, it is therefore highly desirable to provide power sources that are very long lasting without any degradation of their performance—preferably over the practical life of the device—and that can very reliably and rapidly provide adequate enough of electrical energy to power such medical devices.

In the disclosed embodiments of the medical devices such as AEDs, the power sources that are equipped with at least one reserve battery (such as the so-called liquid reserve or thermal battery with shelf life of up to 20 years or even longer) are utilized to ensure that the device can be powered reliably with the required amount of power in emergency situations.

SUMMARY OF THE INVENTION

Accordingly, an automated external defibrillator is provided. The automated external defibrillator comprising: a reserve power source for providing power to defibrillate a patient, the reserve power source comprising: a reserve battery which requires activation to produce power; an activator for activating the reserve power upon one of an electrical or mechanical activation; a pair of terminals operatively connected to the reserve battery for outputting the produced power to electrode pads configured to supply the produced power to a surface of the patient; and a stop for preventing the activator from activating the reserve power source, the stop being selectively removable when activation is desired.

The automated external defibrillator can further comprise conditioning circuitry for conditioning the produced power prior to output at the terminals.

The reserve battery can be a liquid reserve battery. The liquid reserve battery can include an opening, and the activator can comprise a container having a liquid electrolyte contained therein and a member for releasing the liquid electrolyte into the opening upon activation of the member. The container can be disposed in a sealed cavity. The container can be sealed.

The reserve battery can be a thermal battery. The thermal battery can include an opening, and the activator can comprise a flammable material and generates one or more of a spark or flames in the flammable material and providing one of the flames or sparks into the opening. The thermal battery can comprises an opening, and the activator can comprises at least a single part pyrotechnic material that provides one or more of a spark and flames into the opening upon initiation of the pyrotechnic material.

BRIEF DESCRIPTION OF THE DRAWINGS

These and other features, aspects, and advantages of the apparatus of the present invention will become better understood with regard to the following description, appended claims, and accompanying drawings where:

FIG. 9 illustrates a schematic of a typical reserve thermal battery equipped with a piezoelectric igniter for initiating the thermal battery used in power sources for the AED of FIG. 1.

FIG. 10 illustrates a schematic of the cross-section of the view "C" of FIG. 9, showing another embodiment of the thermal battery activation device.

FIG. 11 illustrates a schematic of a reserve thermal battery equipped with an impact and pyrotechnic material based igniter for initiating the thermal battery used in the AED of FIG. 1.

FIG. 12 illustrates a schematic of the cross-section of the view "D" of FIG. 11, showing another embodiment of the thermal battery activation device.

DETAILED DESCRIPTION OF THE PREFERRED EMBODIMENTS

Figure 1:
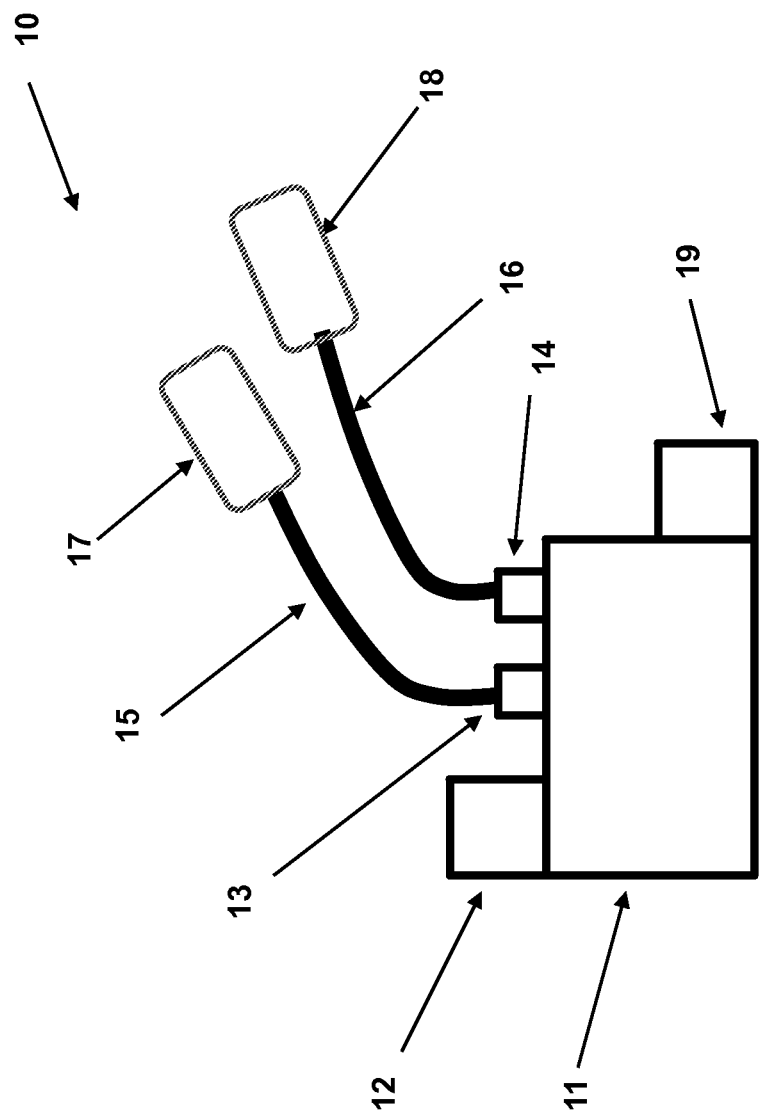
FIG. 1 illustrates a schematic of the first embodiment of the power sources for an AED.

A schematic of a first embodiment 10 of the power source for an AED is shown in FIG. 1. The power source 10 consists of at least one reserve battery 11, such as a thermal battery, with an activation device 12, such as a mechanical initiator (described later in the description) or electrical initiator and terminals 13 and 14. The cables 15 and 16 with corresponding electrode pads 17 and 18, respectively, are then used to transfer any resulting charge to the patient's chest. The terminals 13, 14, cables 15, 16, and electrode pads 17, 18 are shown schematically. The specific configuration thereof is well known in the art of AED devices, such as in U.S. Pat. Nos. 6,041,255 and 6,408,206, the contents of which are incorporated herein by their reference.

In general, depending on the type, voltage level and the amount of electrical power that the reserve batteries 11 can provide, the power source 10 may require power regulation and capacitance storage elements (hereinafter referred to collectively as "conditioning") to provide the proper voltage and current to the electrode pads 17, 18. When the above is the case, the power can be routed from the terminals 13 and 14 via wires (not shown) to the regulation (and if needed capacitance storage) unit 19. The cables 15 and 16 are then output from the regulation unit 19. The conditioning of the electrical power from the reserve batteries is well known in the art.

In the following, the reserve power sources that can be used in the power source 10 of FIG. 1 and initiation methods and devices are described.

Reserve batteries are widely used in military applications, particularly in munitions of various types. Reserve batteries are inactive and inert when manufactured and become active and begin to produce power only when they are activated. Reserve batteries are routinely designed for shelf life of 10-20 years and even longer. Reserve batteries are divided into the following two main types.

A first type includes liquid reserve batteries, in which the electrolyte is stored in a separate compartment such as in a glass ampoule or behind a membrane, etc., and is released into the battery cell when the battery is desired to be activated. In general and for rapid activation, certain means have to be provided to help distribute the electrolyte within the battery cell. Liquid reserve batteries usually use certain mechanism to break the aforementioned glass ampoule or membrane, etc. to release the electrolyte to activate the reserve battery. In many munitions applications, the firing (setback) acceleration is used to break the aforementioned glass ampoule or membrane to release the stored electrolyte to activate the reserve battery. Wicks or spinning of the projectile is then usually used to distribute the electrolyte inside the battery cell.

A second type of reserve batteries are thermal batteries. This class of reserve batteries operates at high temperature. Unlike liquid reserve batteries, in thermal batteries the electrolyte is already in the cells and therefore does not require a distribution mechanism. In thermal batteries, the electrolyte is dry, solid and non-conductive, thereby leaving the battery in a non-operational and inert condition. These batteries incorporate pyrotechnic heat sources to melt the electrolyte just prior to use in order to make them electrically conductive and thereby making the battery active. A common internal pyrotechnic is a blend of Fe and $KClO_4$. Thermal batteries utilize a molten salt to serve as the electrolyte upon activation. The electrolytes can be mixtures of alkali-halide salts and can be used with $Li(Si)/FeS_2$ or $Li(Si)/CoS_2$ couples. Some thermal batteries also employ anodes of $Li(Al)$ in place of the $Li(Si)$ anodes. Insulation and internal heat sinks are used to maintain the electrolyte in its molten and conductive condition during the time of use.

Reserve batteries, particularly thermal batteries have long been used in munitions and other similar applications to provide a relatively large amount of power during a relatively short period of time, mainly during the munitions flight. Thermal batteries have high power density and can provide a large amount of power as long as the electrolyte of the thermal battery stays molten, thereby conductive. The batteries are usually encased in a hermetically-sealed metal container that is usually cylindrical in shape.

Thermal batteries generally use some type of igniter to provide a controlled pyrotechnic reaction to produce output gas, flame or hot particles to ignite the heating elements of the thermal battery. There are currently two distinct classes of igniters that are available for use in thermal batteries. The first class of igniter operates based on electrical energy. Such electrical igniters require electrical energy, such as a separate battery, mechanical to electrical conversion mechanism (such as a crank), or other power sources to operate the electrical igniter and initiate the thermal battery. The second class of igniters, commonly called "inertial igniters", are widely used in gun-fired munitions and operate based on the firing acceleration. In these igniters, the firing (setback) acceleration is generally used to accelerate a "striker mass" to initiate the igniter pyrotechnic material upon impact, generally at provided pinching points. The inertial igniters do not require additional batteries or other power sources for their operation and are thereby often used in high-G munitions applications such as in gun-fired munitions and mortars.

The aforementioned characteristics of liquid reserve and thermal batteries indicate that for most AED applications, thermal batteries can be used as a power source (11 in FIG. 1).

Although thermal batteries are used in the construction of the present power sources 10, those of ordinary skill in the art will appreciate that liquid reserve batteries can also be used.

When being used in an AED device, the battery based power source is highly desirable to be capable of being easily activated without requiring external power sources or requiring the operation of a complex device. The activation device of the battery is also highly desirable to be equipped with safety "locks" such that the battery may not be accidentally activated.

As previously mentioned, liquid reserve batteries are initiated by the release of the electrolyte into the battery cell. The electrolyte is usually stored in a glass ampoule or in a separate compartment and is provided with a membrane or the like in the battery assembly and released into the battery cell by breaking the glass ampoule or rupturing the said membrane. Many other designs of liquid reserve batteries assemblies for keeping the electrolyte out of the battery cell and releasing it into the battery cell are also known in the art. For the present application, the method of activating such liquid reserve thermal batteries is manually and via mechanical actuation. Numerous such mechanical devices of various types can be constructed depending on the liquid reserve battery design. The following are a few types of mechanical liquid reserve battery activation devices.

Figure 2:
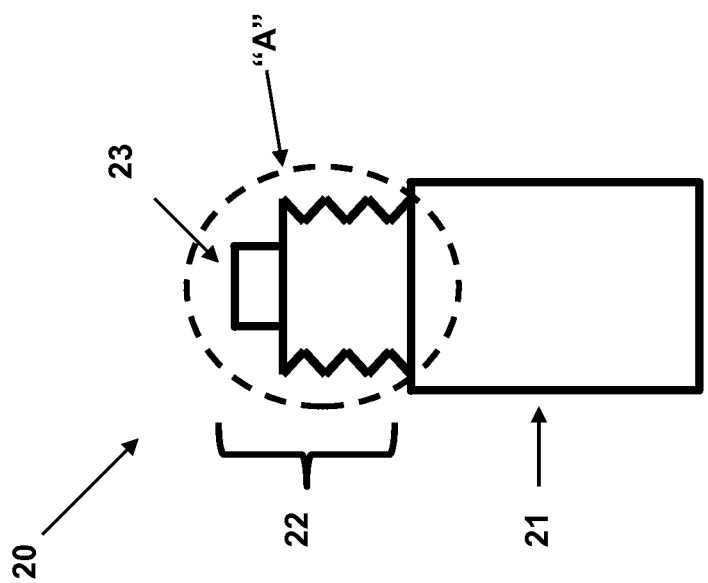
FIG. 2 illustrates a schematic of a typical liquid reserve battery with a mechanical activation mechanism for use in power sources for the AED of FIG. 1.

Consider a basic liquid reserve battery shown by the schematic of FIG. 2. In the schematic of FIG. 2, the liquid reserve battery 20 (no terminals are shown for simplicity) is shown to consist of the battery cell 21 and the compartment 22 (which also includes the mechanical initiation mechanisms 23), in which the liquid electrolyte is stored. Noting that many different liquid electrolyte storage methods and means are possible—many of which are known in the art, and also noting that many different methods and means of releasing the stored electrolyte are possible—also many of which are known in the art, the embodiment that is presented in the schematic of FIG. 2 and is described below is considered to be for illustration purposes only of the characteristics of such liquid reserve battery designs, and is considered to be capable of being constructed with any appropriate means of mechanical activation.

Figure 3:
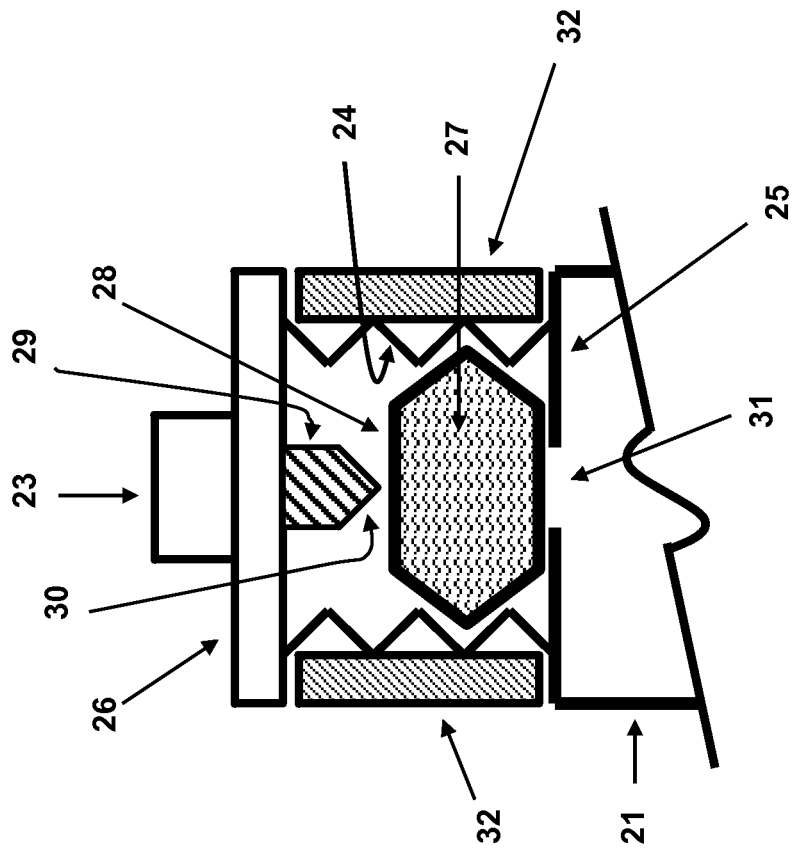
FIG. 3 illustrates a schematic of the cross-section of the view "A" of FIG. 2, showing an embodiment of the electrolyte storage and mechanical activation mechanism that is equipped with an accidental activation prevention mechanism.
Figure 4:
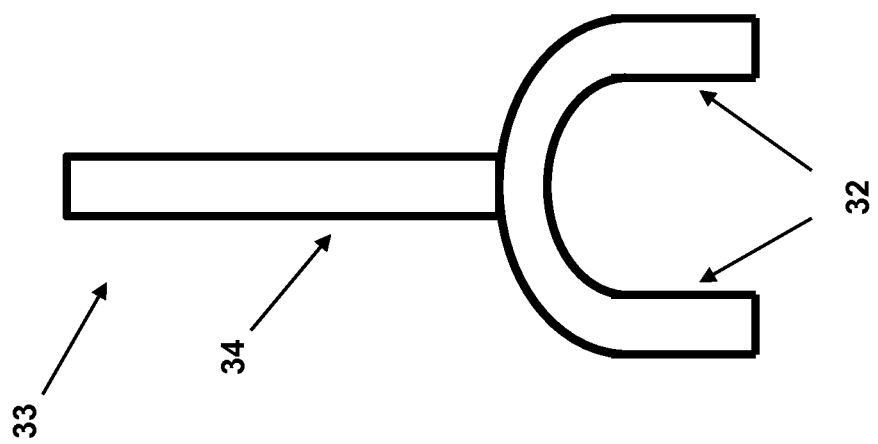
FIG. 4 illustrates a schematic of an accidental activation "pin" for the liquid reserve battery of FIGS. 2 and 3.

In the schematic of FIG. 2, the liquid reserve battery 20, including its cell portion 21 and its electrolyte compartment 22 is considered to be cylindrical in shape, but can take many shapes. The cross-section of the view "A" (FIG. 2) of the aforementioned compartment 22 of the electrolyte storage and mechanical activation mechanism 23 is shown schematically in FIG. 3. The compartment 22 consists of a bellow 24 which is attached on one end to the top cap 25 of the cell portion 21 of the liquid reserve battery and to the top element 26 on the other end. The bellow 24 is preferably welded, soldered or brazed to the top cap 25 and the top element 26 (or attached using any other available method) such that it would form a sealed seam and render the liquid reserve battery 20 hermetically sealed. The liquid electrolyte 27 is considered to be stored in a sealed container 28. A pin element 29 with a sharp tip 30 is fixed to the top element 26 as shown in FIG. 3. A safety pin 33 (FIG. 4) with a handle 34 and a two-prong fork 32 (FIGS. 3 and 4) is generally positioned between the top cap 25 and the top element 26 to prevent accidental activation of the liquid reserve battery 20 as described below.

To activate the liquid reserve battery 20, the user would first pull out the safety pin 33. As a result, the bellow 24 becomes free to displace downwards. The bellow 24 is preferably at or close to its free length with the safety pin 33 in place as shown in FIG. 3 so that it would not suddenly displace downward upon removal of the safety pin 33. To activate the liquid reserve battery, the user must then press down the element 23 (rigid button in this case), thereby causing the bellow 24 to compress, moving the pin element 29 down towards the electrolyte container 28, and eventually pressing the sharp tip 30 of the pin element 29 to the surface of the electrolyte container 28 and causing it to break, if it is made as a glass ampoule, or rupture, if it is made as a relatively thin metal or the like membrane, in which case the pin element 29 is preferably made to be long enough to reach the opposite side of the electrolyte container 28 above the top cap 25 and also rupture the electrolyte container 28 over the hole 31 which is provided in the top cap 25 as shown in FIG. 3. As a result, the electrolyte liquid 27 is released and by the force of gravity would pour into the cell 21 cavity and activate the liquid reserve battery 20.

Figure 5:
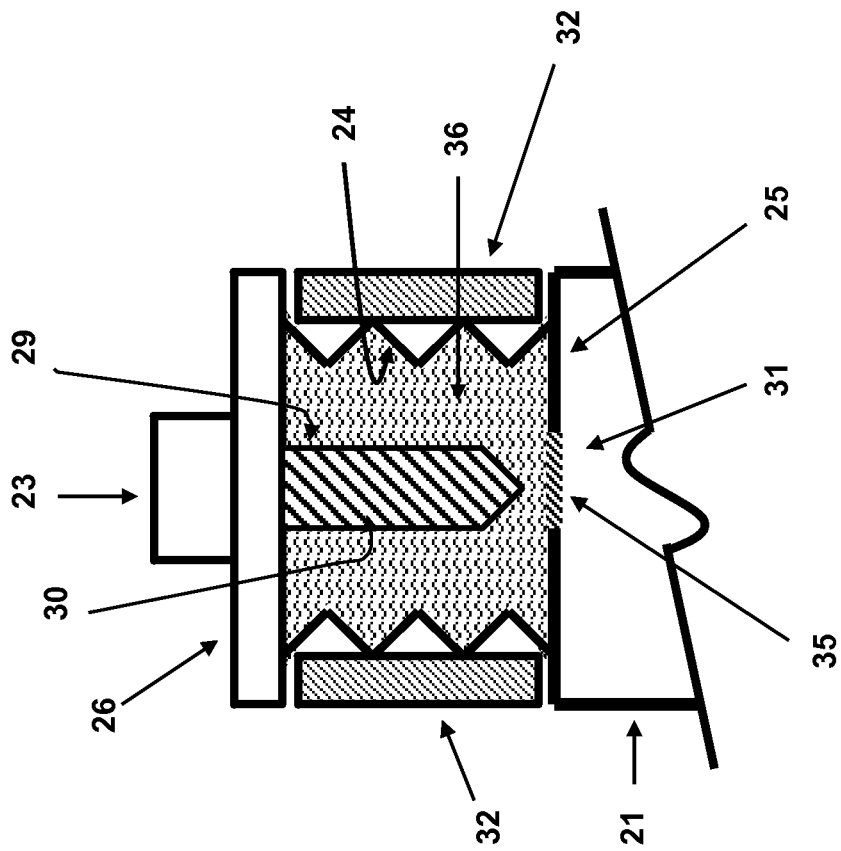
FIG. 5 illustrates a schematic of the cross-section of the view "A" of FIG. 2, showing another embodiment of the electrolyte storage and mechanical activation mechanism that is equipped with an accidental activation prevention mechanism.

Alternatively, the compartment 22 (FIG. 2) can be constructed as shown in the schematic of the cross-section view shown in FIG. 5 (replacing the view "A" of FIG. 2 shown in FIG. 3). In this embodiment, the compartment 22 consists of the bellow 24 which is attached on one end to the top cap 25 of the cell portion 21 of the liquid reserve battery and to the top element 26 on the other end. The bellow 24 is preferably welded, soldered or brazed to the top cap 25 and the top element 26 (or attached using any other available method) such that it would form a sealed seam and render the liquid reserve battery 20 hermetically sealed. The hole 31 which is provided in the top cap 25 is covered by a membrane 35 to seal the hole 31. The volume inside the bellow 24 is filled with the liquid electrolyte 36, with the membrane 35 ensuring that the liquid electrolyte 36 would not leak into the interior of the cell 21 of the liquid reserve battery 20. The pin element 29 with a sharp tip 30 is still fixed to the top element 26 as shown in FIG. 5. A safety pin 33 (FIG. 4) with a handle 34 and a two-prong fork 32 (FIGS. 4 and 5) is generally positioned between the top cap 25 and the top element 26 to prevent accidental activation of the liquid reserve battery 20 as described below.

To activate the liquid reserve battery 20, the user would first pull out the safety pin 33. As a result, the bellow 24 becomes free to displace downwards. The bellow 24 is preferably at or close to its free length with the safety pin 33 in place as shown in FIG. 5 so that it would not suddenly travel downward upon removal of the safety pin 33. To activate the liquid reserve battery, the user must then press down the element 23 (rigid button in this case), thereby causing the bellow 24 to compress, moving the pin element 29 down towards the membrane 35, and eventually pressing the sharp tip 30 of the pin element 29 and puncturing the membrane 35. Once the user releases the bellow 24, the electrolyte liquid 36 would freely flow into the cell 21 cavity by the force of gravity and/or the pressure exerted on the element 23, and activates the liquid reserve battery 20.

It is appreciated by those skilled in the art that the element 23 is not necessary for the embodiments of FIGS. 2-5. The element 23 may, however, be constructed with a lever mechanism connecting the top element 26 to the body of the cell 21, thereby providing for mechanical advantage to amplify the force applied by the user to drive the pin element 29 down to release the liquid electrolyte 27 and 36 of FIGS. 3 and 5, respectively. Many such lever type mechanisms are well known in the art and can be used in the embodiments of FIGS. 2-5.

Alternatively, the bellow 24 may be preloaded in tension in the configuration shown in FIGS. 3 and 5 with the safety pin 33 in place. The said tensile preloading may be provided by the flexibility of the bellow 24 or by additional helical springs (not shown) that are attached to the top cap 25 on one side and to the top element 26 on the other. The helical spring may be positioned either inside or outside the bellow 24.

Figure 6:
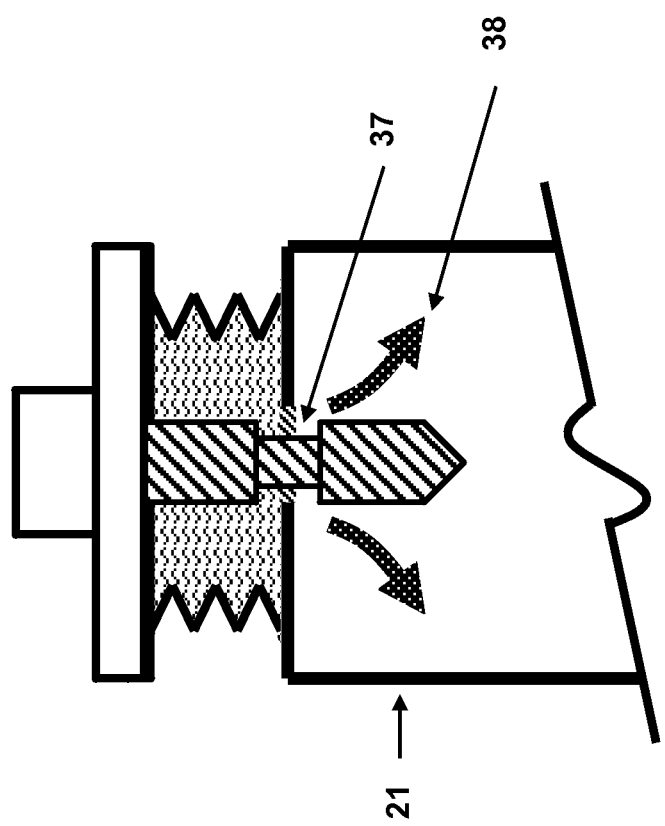
FIG. 6 illustrates a schematic of the electrolyte storage and activation mechanism portion of the liquid reserve battery of FIG. 1 after rupture of the membrane to release the electrolyte into the battery cell for activation.

For such embodiment, the user can activate the liquid reserve battery 20 by simply pulling the safety pin 33 out. The tensile preloading will then force the bellow 24 to displace downwards, moving the pin element 29 down towards the membrane 35, and eventually pressing the sharp tip 30 of the pin element 29 against the membrane 35 and puncturing it. The stem 37 of the pin element 29 behind its sharp tip 30 is preferably provided with a narrow section so that after the sharp tip 30 has passed through the membrane 35 as shown in FIG. 6, the electrolyte liquid 36 can more freely flow into the cell 21 cavity by the force of gravity and/or by the aforementioned tensile preloading of the bellow 24 and activates the liquid reserve battery 20.

Figure 7:
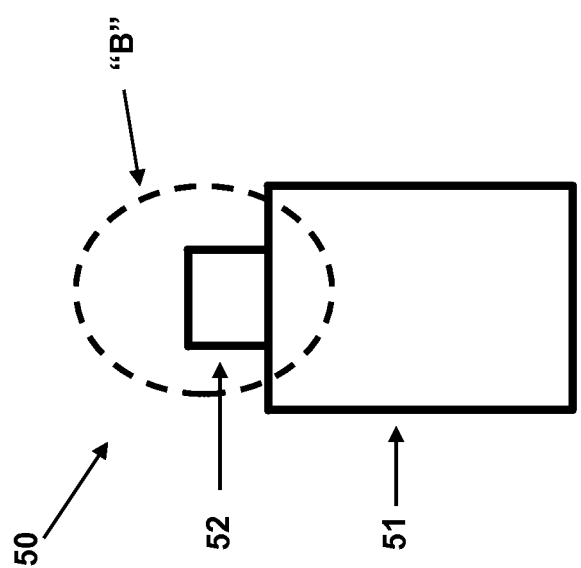
FIG. 7 illustrates a schematic of a typical reserve thermal battery with an electrically initiated igniter for use in power sources for the AED of FIG. 1.

In an embodiment of the power source 10, FIG. 1, the reserve battery 11 can be a thermal battery. The basic structure of a typical reserve thermal battery is shown in the schematic of FIG. 7 (again, the terminals and cables are not shown for simplicity). In the schematic of FIG. 7, the reserve thermal battery 50 includes the battery cell 51 and the compartment 52, which includes the battery initiation device. As previously described, two basic types of initiators are commonly use and may also be used to activate thermal batteries, i.e., to ignite their so-called heat pallets, namely electrical initiators and those that rely on impact (and generally local temperature rise at the site of impact) at pinching points in (one part or two part) pyrotechnic materials.

A third type of initiator that can also be used to similarly initiate the present thermal batteries consist of the use of piezoelectric materials to generate a relatively high voltage upon sudden application of force (impact force) to provide a spark to activate the thermal battery.

The disclosed power source 10, may use either one (or combination) of the above three types of initiation mechanisms to activate the device reserve (in this case thermal) battery 11.

In the schematic of FIG. 7, the reserve thermal battery 50 (no power source terminals are shown), including its battery cell portion 51 and the compartment 52 which houses the battery initiation (activation) elements are shown. The thermal batteries are generally designed in cylindrical shapes mainly from heat retention and manufacturing considerations, but may be formed in almost any other practical shapes. In the following description, thermal batteries with the aforementioned three initiation options are described. It is, however, appreciated by those skilled in the art that more than one initiator of one type or different types may also be used (such as being assembled in the compartment 52) to ensure reliability of thermal battery activation and the ease with which the thermal battery can be activated by the user.

Figure 8:
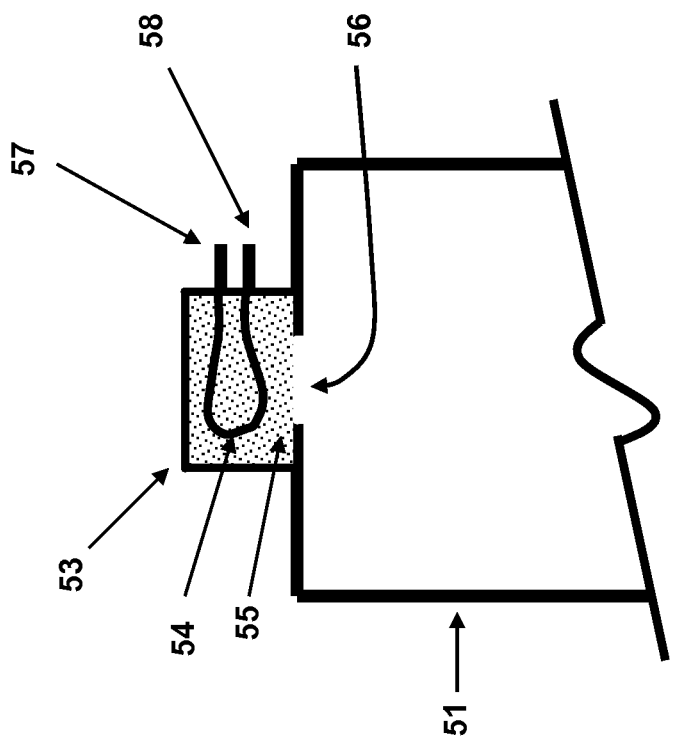
FIG. 8 illustrates a schematic of the cross-section of the view "B" of FIG. 7, showing a preferred embodiment of the thermal battery activation device.

In one embodiment, the thermal battery 50 is activated electrically using an electrical initiator 53 (igniter) mounted in the compartment 52 as shown in the cross-section of the view "B" (FIG. 7) shown in FIG. 8. Such electrical igniters are well known in the art and usually consist of a heating wire (heating element) 54, which is heated by an electrical current (the so-called electric match). In FIG. 8, the terminals 57 and 58 are considered to be for connection to the aforementioned power source that is used to activate the thermal battery. The heating element 54 is usually surrounded by pyrotechnic or other easy to ignite material 55 that are first ignited by the heating element 54 and generate flames and spark that enter the thermal battery cell to initiate the battery heat pallets through a provided opening 56 as shown in FIG. 8.

Alternatively, the heating element 54 of the electrical igniter 53 is positioned inside the thermal battery cell and is in direct contact with the heat pallets of the thermal battery via certain easier to ignite medium such as the so-called heat paper.

In this embodiment, an outside power source is required to supply the required current to the electrical igniter 53 to activate the thermal battery 50. Electric igniters require very small amount of electrical energy to ignite their pyrotechnic material (the amount of electrical energy may be as low as 3-4 milli-Joules). In such cases, the electrical igniter 53 may be powered by a battery for thermal battery activation.

Where a battery is provided for thermal battery activation, considering the goal of eliminating the need for any type of power source other than very long lasting and highly reliable reserve (liquid reserve and thermal) batteries, such option is not preferred unless a similarly very long lasting (low power) battery that can provide enough power to ignite an electrical initiator is used.

Alternatively, a piezoelectric-based power generator may be used to generate enough electrical energy to power the electrical igniter 53 to activate the thermal battery. Such piezoelectric-based generators have been described in U.S. Pat. Nos. 7,312,557; 7,701,120, the disclosures of which are incorporated herein by reference.

In the embodiment 50 of FIG. 7 and for the aforementioned type of initiators used to activate the thermal battery, a safety pin or cap or switch (not shown) can be used to prevent unintended activation of the thermal battery. Such devices for preventing unintended actuation of a switch or caps that have to be removed or displaced to access activation switches or levers are well known in the art and may be used for this purpose.

In another embodiment, an aforementioned piezoelectric type of initiator (hereinafter referred to as "piezo initiator") is used to activate the thermal battery by generating sparks upon actuation. Piezoelectric ignition is a type of ignition that is commonly used in gas stoves, portable camping stoves, gas grills and some other types of lighters. It consists of a small, spring-loaded hammer which, when a button is pressed, hits a crystal of piezoelectric element (PZT) or quartz crystal. This sudden forceful deformation (impact) produces a high voltage and subsequent electrical discharge, which ignites the gas.

In this embodiment 60, a "piezo initiator" 61 is attached to the thermal battery cell 62 as shown in the schematic of FIG. 9. For the sake of simplicity, a button type "piezo igniter" (button indicated by numeral 63) is shown in the schematic of FIG. 9. The schematic of the cross-section of the view "C" (FIG. 9) shown in FIG. 10. In FIG. 10, the "piezo initiator" portion 61 is shown to consist of a chamber 64, in which certain pyrotechnic material with or without certain intermediate and more easily ignited material such as the so-called heat papers 65 is provided.

To activate the thermal battery 60, the user would press on the "piezo igniter" button 63, thereby causing the igniter to generate an electrical discharge 66, which would in turn ignite the pyrotechnic material 65. The flame and sparks generated by the pyrotechnic material 65 would then enter the thermal battery cell 62 through the provided hole 67, and ignite the thermal battery heat pallets. As previously indicated, intermediate materials such as heat papers may also be provided inside the thermal battery cell 62 to help and ensure that the thermal battery heat pallets are ignited.

In another embodiment 70, which is shown schematically in FIG. 11, employs an impact based initiator 71 to initiate the thermal battery. The basic mechanism of operation of this initiator is similar to the aforementioned "inertial igniters", with the difference being that the impact is achieved by a spring that is preloaded and then released by pushing a button (similar to the aforementioned "piezo igniter"), pulling a lever or handle (to preload a spring in tension or compression and then release it upon further pulling of the lever or handle), or rotation of a lever (to similarly preload a spring in either tension or compression and then release it upon further rotation of the lever), or the like. A "hammer" or "striker mass" is attached to the releasing end of the spring and is thereby released upon the release of the spring. The "hammer" or "striker mass" would then strike an "anvil" (a base striking element). One part or two part pyrotechnic materials are at the point of impact, preferably as provided protrusions on one or preferably both surfaces, thereby pinching the pyrotechnic material(s) between the pinching points during the impact, and thereby initiating the pyrotechnic material. The flame and sparks generated by the ignited pyrotechnic material is then guided through provided ports into the thermal battery cell to ignite the heat pallets in the thermal batter (directly or via other easy to ignite materials such as the so-called heat papers).

In the schematic of the embodiment 70, which is shown schematically in FIG. 11, an impact based initiator 71 is used for activation of the thermal battery. The cross-section of the view "D" (FIG. 11) of the impact based initiator 71 is shown schematically in FIG. 12. The impact based initiator 71 is shown to consist of an impact generating component 73 (in this case and as an example, a button type—similar to that of 63 for the "piezo-igniter" of the embodiment of FIGS. 9 and 10), with an impact hammer 74. The anvil portion is the base of the housing 77, which is provided with a protrusion 76, which faces the tip (protrusion) 75 of the hammer 74. A one part pyrotechnic material 78 is provided over and around the protrusion 76. If a two part pyrotechnic material is used, then one part will be used to cover the protrusion 75 and the other part will be used to cover the protrusion 76.

To activate the thermal battery 70, the user would press on the button 73 (the impact generating component of the initiator 71), thereby causing the spring in the impact generating initiator (not shown) to compress (or extend) and then release and thereby propel the impact hammer 74 forwards towards the pyrotechnic material 78. The tip 75 of the impact hammer 74 will then impact over the protrusion 76 on the base of the housing 77, thereby pinching a portion of the pyrotechnic material 78 between the protrusions 75 and 76, thereby causing it to ignite. The pyrotechnic material 78 is thereby ignited. The resulting flames and sparks would then enter the thermal battery cell 72 through the provided hole 79 provided into the thermal battery cell, and ignite the thermal battery heat pallets. As previously indicated, intermediate materials such as heat papers may also be provided inside the thermal battery cell 72 and/or inside the housing 77 to help and ensure that the thermal battery heat pallets are ignited.

It is appreciated by those skilled with the art that the disclosed power source 10 for AED's may be provided with more than one reserve power source, which may be a combination of different types of reserve power sources such as a combination of at least one liquid reserve battery and at least one thermal battery. Alternatively, the disclosed power source 10 for AED's may also be provided with rechargeable batteries and/or capacitors that are kept charged by a building power supply so that the reserve batteries (liquid reserve and/or thermal battery) are used only if the rechargeable batteries and/or capacitors used are discharged to the point that they cannot provide enough power for the intended use of the AED. In any of the above combinations, the entire power source and its components shown in FIG. 1 can be used.

The regulation unit 19 consists of the one of the commonly used electrical and electronics circuitries that are used to condition the voltage and current (power) output of the at least one (liquid or thermal) reserve batteries 11 to match the requirements for an AED. The unit 19 may also use at least one relatively high capacitance capacitor to allow the power source 10 to output enough current to enable it to supply the required charge. Such capacitors may be necessary to allow the use of relatively smaller reserve batteries and extend the amount of time that the power source 10 is capable of being used to defibrillate the patient. Such capacitors may particularly be required when liquid reserve are used in the power source 10, since unlike thermal batteries, such batteries are usually not capable of providing high currents.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A power supply comprising:
a reserve power source for providing power, the reserve power source comprising:
a liquid reserve battery which requires activation to produce power;
an activator having a liquid electrolyte for activating the liquid reserve battery upon a mechanical activation of the activator such that the liquid electrolyte is forced from the activator into the liquid reserve battery through a communication between the activator and the liquid reserve battery;
a pair of terminals operatively connected to the liquid reserve battery for outputting the produced power; and
a mechanical stop for preventing the activator from activating the liquid reserve battery, the stop being selectively removable when activation is desired;
wherein the activator comprises a container having the liquid electrolyte contained therein and the activator further comprises:
a top; and
a bellow attached on one end to the top and to a portion of the liquid reserve battery at an other end.

2. The power supply of claim 1, further comprising conditioning circuitry for conditioning the produced power prior to output at the terminals.

3. The power supply of claim 1, wherein the bellow is the container and the bellow is sealed to the top at the one end and to the portion of the liquid reserve battery at the other end.

4. The power supply of claim 1, wherein the bellow contains the container and at least the container is sealed.

5. The power supply of claim 1, wherein the portion of the liquid reserve battery comprises a hole covered by a membrane to seal the hole.

6. The power supply of claim 5, wherein the activator further comprises a pin element attached to the top element such that activation of the activator causes the pin element to open the membrane covering the hole to provide the communication between the activator and the liquid reserve battery.

7. The power supply of claim 6, wherein the top element is configured to force the liquid electrolyte through the opened membrane covering the hole upon activation of the activator.

8. The power supply of claim 1, wherein the activator includes an impact surface for facilitating mechanical activation of the activator upon application of an impact force on the impact surface.

9. The power supply of claim 1, wherein the mechanical stop comprises a member positioned between the top and the portion of the liquid reserve battery.

10. The power supply of claim 1, further comprising a biasing member for biasing the top towards the portion of the liquid reserve battery and wherein the mechanical stop comprises a member positioned between the top and the portion of the liquid reserve battery.

11. The power supply of claim 10, wherein the biasing member is the bellows.

12. A power supply comprising:
   a reserve power source for providing power, the reserve power source comprising:
      a liquid reserve battery which requires activation to produce power;
      an activator having a liquid electrolyte for activating the liquid reserve battery upon a mechanical activation of the activator such that the liquid electrolyte is forced from the activator into the liquid reserve battery through a communication between the activator and the liquid reserve battery;
      a pair of terminals operatively connected to the liquid reserve battery for outputting the produced power; and
   a mechanical stop for preventing the activator from activating the liquid reserve battery, the stop being selectively removable when activation is desired;
   wherein the mechanical stop comprises a member positioned between a surface of the activator and a surface of the liquid reserve battery for preventing the activator from activating the liquid reserve battery and the member comprises a safety pin having two prongs, the two prongs being positioned between the surface of the activator and the surface of the liquid reserve battery.

* * * * *